US012746413B2

(12) United States Patent
Cannata et al.

(10) Patent No.: US 12,746,413 B2
(45) Date of Patent: Sep. 29, 2026

(54) HISTOTRIPSY EXCITATION SEQUENCES OPTIMIZED FOR BUBBLE CLOUD FORMATION USING SHOCK SCATTERING

(71) Applicants: HISTOSONICS, INC., Plymouth, MN (US); THE REGENTS OF THE UNIVERSITY OF MICHIGAN, Ann Arbor, MI (US)

(72) Inventors: Jonathan M. Cannata, Ann Arbor, MI (US); Timothy L. Hall, Ann Arbor, MI (US); Adam D. Maxwell, Ann Arbor, MI (US); Dejan Teofilovic, Ann Arbor, MI (US)

(73) Assignees: HISTOSONICS, INC., Plymouth, MN (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 18/737,746

(22) Filed: Jun. 7, 2024

(65) Prior Publication Data

US 2024/0316367 A1 Sep. 26, 2024

Related U.S. Application Data

(63) Continuation of application No. 16/410,821, filed on May 13, 2019, which is a continuation of application
(Continued)

(51) Int. Cl.
*A61N 7/00* (2006.01)
*A61B 17/00* (2006.01)
(Continued)

(52) U.S. Cl.
CPC .......... *A61N 7/00* (2013.01); *A61B 17/22004* (2013.01); *A61B 2017/00176* (2013.01);
(Continued)

(58) Field of Classification Search
CPC .............. A61N 7/00; A61N 2007/0039; A61N 2007/0078; A61B 17/22004;
(Continued)

(56) References Cited

U.S. PATENT DOCUMENTS

| | | | |
|---|---|---|---|
| 3,243,497 | A | 3/1966 | Kendall et al. |
| 3,679,021 | A | 7/1972 | Goldberg et al. |

(Continued)

FOREIGN PATENT DOCUMENTS

| | | | |
|---|---|---|---|
| CA | 2910561 | C | 7/2021 |
| CA | 2908740 | C | 10/2021 |

(Continued)

OTHER PUBLICATIONS

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

(Continued)

*Primary Examiner* — Hien N Nguyen
(74) *Attorney, Agent, or Firm* — Shay Glenn LLP

(57) ABSTRACT

Methods and devices for producing cavitation in tissue are provided. In one embodiment, a shock scattering method of Histotripsy therapy comprises delivering an initiation pressure waveform from an ultrasound therapy transducer into tissue, the initiation pressure waveform being configured to produce at least one bubble in the tissue, delivering a scattering pressure waveform from the ultrasound therapy transducer into the at least one bubble within a life-cycle of the at least one bubble, and producing cavitation nuclei near the at least one bubble with the scattering pressure waveform. The scattering pressure waveform can be delivered during the life-cycle of the at least one bubble. In some embodiments, the scattering pressure waveform is delivered
(Continued)

within 5 μs to 1 s of the initiation pressure waveform. Systems for performing shock scattering Histotripsy therapy are also discussed.

10 Claims, 8 Drawing Sheets

Related U.S. Application Data

No. 14/323,693, filed on Jul. 3, 2014, now Pat. No. 10,293,187.

(60) Provisional application No. 61/842,820, filed on Jul. 3, 2013.

(51) Int. Cl.
*A61B 17/22* (2006.01)
*A61B 17/225* (2006.01)

(52) U.S. Cl.
CPC ............... *A61B 2017/22008* (2013.01); *A61B 2017/22028* (2013.01); *A61B 17/225* (2013.01); *A61N 2007/0039* (2013.01); *A61N 2007/0078* (2013.01)

(58) Field of Classification Search
CPC ........ A61B 17/225; A61B 2017/00176; A61B 2017/22008; A61B 2017/22028
See application file for complete search history.

(56) References Cited

U.S. PATENT DOCUMENTS 3,693,415 A 9/1972 Whittington
3,879,699 A 4/1975 Pepper
4,016,749 A 4/1977 Wachter
4,024,501 A 5/1977 Herring et al.
4,051,394 A 9/1977 Tieden
4,114,457 A 9/1978 Thun
4,117,446 A 9/1978 Alais
4,266,747 A 5/1981 Souder, Jr. et al.
4,269,174 A 5/1981 Adair
4,277,367 A 7/1981 Madsen et al.
4,351,038 A 9/1982 Alais
4,406,153 A 9/1983 Ophir et al.
4,440,025 A 4/1984 Hayakawa et al.
4,447,031 A 5/1984 Souder, Jr. et al.
4,453,408 A 6/1984 Clayman
4,483,343 A 11/1984 Beyer et al.
4,483,345 A 11/1984 Miwa
4,548,374 A 10/1985 Thompson et al.
4,549,533 A 10/1985 Cain et al.
4,550,606 A 11/1985 Drost
4,551,794 A 11/1985 Sandell
4,575,330 A 3/1986 Hull
4,622,972 A 11/1986 Giebeler, Jr.
4,625,731 A 12/1986 Quedens et al.
4,641,378 A 2/1987 McConnell et al.
4,669,483 A 6/1987 Hepp et al.
4,689,986 A 9/1987 Carson et al.
4,757,820 A 7/1988 Itoh
4,791,915 A 12/1988 Barsotti et al.
4,819,621 A 4/1989 Ueberle et al.
4,829,491 A 5/1989 Saugeon et al.
4,856,107 A 8/1989 Dory
4,865,042 A 9/1989 Umemura et al.
4,888,746 A 12/1989 Wurster et al.
4,890,267 A 12/1989 Rudolph
4,922,917 A 5/1990 Dory
4,928,672 A 5/1990 Grasser et al.
4,938,217 A 7/1990 Lele
4,957,099 A 9/1990 Hassler
4,973,980 A 11/1990 Howkins et al.
4,984,575 A 1/1991 Uchiyama et al.
4,991,151 A 2/1991 Dory
4,995,012 A 2/1991 Dory
RE33,590 E 5/1991 Dory
5,014,686 A 5/1991 Schafer
5,065,751 A 11/1991 Wolf
5,078,140 A 1/1992 Kwoh
5,080,101 A 1/1992 Dory
5,080,102 A 1/1992 Dory
5,091,893 A 2/1992 Smith et al.
5,092,336 A 3/1992 Fink
5,097,709 A 3/1992 Masuzawa et al.
5,111,822 A 5/1992 Dory
5,143,073 A 9/1992 Dory
5,143,074 A 9/1992 Dory
5,150,711 A 9/1992 Dory
5,158,070 A 10/1992 Dory
5,158,071 A 10/1992 Umemura et al.
5,163,421 A 11/1992 Bernstein et al.
5,165,412 A 11/1992 Okazaki
5,174,294 A 12/1992 Saito et al.
5,195,509 A 3/1993 Rentschler et al.
5,209,221 A 5/1993 Riedlinger
5,215,680 A 6/1993 D'Arrigo
5,219,401 A 6/1993 Cathignol et al.
5,222,806 A 6/1993 Roberts
5,230,340 A 7/1993 Rhyne
5,295,484 A 3/1994 Marcus et al.
5,316,000 A 5/1994 Chapelon et al.
5,354,258 A 10/1994 Dory
5,380,411 A 1/1995 Schlief
5,393,296 A 2/1995 Rattner
5,409,002 A 4/1995 Pell
5,431,621 A 7/1995 Dory
5,435,311 A 7/1995 Umemura et al.
5,443,069 A 8/1995 Schaetzle
5,450,305 A 9/1995 Boys et al.
5,469,852 A 11/1995 Nakamura et al.
5,474,071 A 12/1995 Chapelon et al.
5,474,531 A 12/1995 Carter
5,490,051 A 2/1996 Messana
5,492,126 A 2/1996 Hennige et al.
5,501,655 A 3/1996 Rolt et al.
5,520,188 A 5/1996 Hennige et al.
5,523,058 A 6/1996 Umemura et al.
5,524,620 A 6/1996 Rosenschein
5,524,875 A 6/1996 Thommen, Jr.
5,540,909 A 7/1996 Schutt
5,542,935 A 8/1996 Unger et al.
5,558,092 A 9/1996 Unger et al.
5,563,346 A 10/1996 Bartelt et al.
5,566,675 A 10/1996 Li et al.
5,573,497 A 11/1996 Chapelon
5,580,575 A 12/1996 Unger et al.
5,582,578 A 12/1996 Zhong et al.
5,590,657 A 1/1997 Cain et al.
5,601,526 A 2/1997 Chapelon et al.
5,617,862 A 4/1997 Cole et al.
5,648,098 A 7/1997 Porter
5,665,054 A 9/1997 Dory
5,666,954 A 9/1997 Chapelon et al.
5,676,452 A 10/1997 Scholz
5,676,692 A 10/1997 Sanghvi et al.
5,678,554 A 10/1997 Hossack et al.
5,683,064 A 11/1997 Copeland et al.
5,694,936 A 12/1997 Fujimoto et al.
5,695,460 A 12/1997 Siegel et al.
5,717,657 A 2/1998 Ruffa
5,720,287 A 2/1998 Chapelon et al.
5,724,972 A 3/1998 Petrofsky
5,743,863 A 4/1998 Chapelon
5,753,929 A 5/1998 Bliss
5,759,162 A 6/1998 Oppelt et al.
5,766,138 A 6/1998 Rattner
5,769,790 A 6/1998 Watkins et al.
5,797,848 A 8/1998 Marian et al.
5,800,365 A 9/1998 Zhong et al.
5,820,623 A 10/1998 Ng
5,823,962 A 10/1998 Schaetzle et al.
5,827,204 A 10/1998 Grandia et al.

(56) References Cited

U.S. PATENT DOCUMENTS

| | | | |
|---|---|---|---|
| 5,836,896 | A | 11/1998 | Rosenschein |
| 5,849,727 | A | 12/1998 | Porter et al. |
| 5,873,902 | A | 2/1999 | Sanghvi et al. |
| 5,879,314 | A | 3/1999 | Peterson et al. |
| 5,928,169 | A | 7/1999 | Schitzle et al. |
| 5,932,807 | A | 8/1999 | Mallart |
| 5,947,904 | A | 9/1999 | Hossack et al. |
| 6,001,069 | A | 12/1999 | Tachibana et al. |
| 6,007,499 | A | 12/1999 | Martin et al. |
| 6,022,309 | A | 2/2000 | Celliers et al. |
| 6,036,667 | A | 3/2000 | Manna et al. |
| 6,065,166 | A | 5/2000 | Sharrock et al. |
| 6,088,613 | A | 7/2000 | Unger |
| 6,093,883 | A | 7/2000 | Sanghvi et al. |
| 6,113,558 | A | 9/2000 | Rosenschein et al. |
| 6,126,607 | A | 10/2000 | Whitmore, III et al. |
| 6,128,958 | A | 10/2000 | Cain |
| 6,143,018 | A | 11/2000 | Beuthan et al. |
| 6,165,144 | A | 12/2000 | Talish et al. |
| 6,176,842 | B1 | 1/2001 | Tachibana et al. |
| 6,296,619 | B1 | 10/2001 | Brisken et al. |
| 6,308,585 | B1 | 10/2001 | Nilsson et al. |
| 6,308,710 | B1 | 10/2001 | Silva |
| 6,309,355 | B1 | 10/2001 | Cain et al. |
| 6,318,146 | B1 | 11/2001 | Madsen et al. |
| 6,321,109 | B2 | 11/2001 | Ben-Haim et al. |
| 6,338,566 | B1 | 1/2002 | Verdier |
| 6,344,489 | B1 | 2/2002 | Spears |
| 6,391,020 | B1 | 5/2002 | Kurtz et al. |
| 6,413,216 | B1 | 7/2002 | Cain et al. |
| 6,419,648 | B1 | 7/2002 | Vitek et al. |
| 6,424,885 | B1 | 7/2002 | Niemeyer et al. |
| 6,470,204 | B1 | 10/2002 | Uzgiris et al. |
| 6,488,639 | B1 | 12/2002 | Ribault et al. |
| 6,490,469 | B2 | 12/2002 | Candy |
| 6,500,141 | B1 | 12/2002 | Irion et al. |
| 6,506,154 | B1 | 1/2003 | Ezion et al. |
| 6,506,171 | B1 | 1/2003 | Vitek et al. |
| 6,508,774 | B1 | 1/2003 | Acker et al. |
| 6,511,428 | B1 | 1/2003 | Azuma et al. |
| 6,511,444 | B2 | 1/2003 | Hynynen et al. |
| 6,522,142 | B1 | 2/2003 | Freundlich |
| 6,524,251 | B2 | 2/2003 | Rabiner et al. |
| 6,536,553 | B1 | 3/2003 | Scanlon |
| 6,543,272 | B1 | 4/2003 | Vitek |
| 6,556,750 | B2 | 4/2003 | Constantino et al. |
| 6,559,644 | B2 | 5/2003 | Froundlich et al. |
| 6,576,220 | B2 | 6/2003 | Unger |
| 6,599,288 | B2 | 7/2003 | Maguire et al. |
| 6,607,498 | B2 | 8/2003 | Eshel |
| 6,612,988 | B2 | 9/2003 | Maor et al. |
| 6,613,004 | B1 | 9/2003 | Vitek et al. |
| 6,613,005 | B1 | 9/2003 | Friedman et al. |
| 6,626,854 | B2 | 9/2003 | Friedman et al. |
| 6,626,855 | B1 | 9/2003 | Weng et al. |
| 6,645,162 | B2 | 11/2003 | Friedman et al. |
| 6,648,839 | B2 | 11/2003 | Manna et al. |
| 6,666,833 | B1 | 12/2003 | Friedman et al. |
| 6,685,640 | B1 | 2/2004 | Fry et al. |
| 6,685,657 | B2 | 2/2004 | Jones |
| 6,705,994 | B2 | 3/2004 | Vortman et al. |
| 6,719,449 | B1 | 4/2004 | Laughlin, Jr. et al. |
| 6,719,694 | B2 | 4/2004 | Weng et al. |
| 6,735,461 | B2 | 5/2004 | Vitek et al. |
| 6,736,814 | B2 | 5/2004 | Manna et al. |
| 6,750,463 | B1 | 6/2004 | Riley |
| 6,770,031 | B2 | 8/2004 | Hynynen et al. |
| 6,773,401 | B1 | 8/2004 | Dreschel et al. |
| 6,775,438 | B1 | 8/2004 | Gaedke et al. |
| 6,788,977 | B2 | 9/2004 | Fenn et al. |
| 6,790,180 | B2 | 9/2004 | Vitek |
| 6,820,160 | B1 | 11/2004 | Allman |
| 6,852,082 | B2 | 2/2005 | Strickberger et al. |
| 6,869,439 | B2 | 3/2005 | White et al. |
| 6,890,332 | B2 | 5/2005 | Truckal et al. |
| 6,929,609 | B2 | 8/2005 | Asafusa |
| 7,004,282 | B2 | 2/2006 | Manna et al. |
| 7,059,168 | B2 | 6/2006 | Hibi et al. |
| 7,128,711 | B2 | 10/2006 | Medan et al. |
| 7,128,719 | B2 | 10/2006 | Rosenberg |
| 7,175,596 | B2 | 2/2007 | Vitek et al. |
| 7,175,599 | B2 | 2/2007 | Hynynen et al. |
| 7,196,313 | B2 | 3/2007 | Quinones |
| 7,223,238 | B2 | 5/2007 | Swanbom |
| 7,223,239 | B2 | 5/2007 | Schulze et al. |
| 7,258,674 | B2 | 8/2007 | Cribbs et al. |
| 7,273,458 | B2 | 9/2007 | Prausnitz et al. |
| 7,273,459 | B2 | 9/2007 | Desilets et al. |
| 7,300,414 | B1 | 11/2007 | Holland et al. |
| 7,311,679 | B2 | 12/2007 | Desilets et al. |
| 7,331,951 | B2 | 2/2008 | Eshel et al. |
| 7,341,569 | B2 | 3/2008 | Soltani et al. |
| 7,347,855 | B2 | 3/2008 | Eshel et al. |
| 7,358,226 | B2 | 4/2008 | Dayton et al. |
| 7,359,640 | B2 | 4/2008 | Onde et al. |
| 7,367,948 | B2 | 5/2008 | O'Donnell et al. |
| 7,374,551 | B2 | 5/2008 | Liang et al. |
| 7,377,900 | B2 | 5/2008 | Vitek et al. |
| 7,429,249 | B1 | 9/2008 | Winder et al. |
| 7,431,704 | B2 | 10/2008 | Babaev |
| 7,442,168 | B2 | 10/2008 | Novak et al. |
| 7,462,488 | B2 | 12/2008 | Madsen et al. |
| 7,559,905 | B2 | 7/2009 | Kagosaki et al. |
| 7,656,638 | B2 | 2/2010 | Laakso et al. |
| 7,695,437 | B2 | 4/2010 | Quistgaard et al. |
| 7,714,481 | B2 | 5/2010 | Sakai |
| 7,771,359 | B2 | 8/2010 | Adam |
| 7,967,763 | B2 | 6/2011 | Deem et al. |
| 8,057,408 | B2 | 11/2011 | Cain et al. |
| 8,295,912 | B2 | 10/2012 | Gertner |
| 8,333,115 | B1 | 12/2012 | Garvey et al. |
| 8,337,407 | B2 | 12/2012 | Quistgaard et al. |
| 8,342,467 | B2 | 1/2013 | Stachowski et al. |
| 8,376,970 | B2 | 2/2013 | Babaev |
| 8,539,813 | B2 | 9/2013 | Cain et al. |
| 8,568,339 | B2 | 10/2013 | Rybyanets |
| 8,636,664 | B2 | 1/2014 | Brannan |
| 8,715,187 | B2 | 5/2014 | Landberg Davis et al. |
| 8,845,537 | B2 | 9/2014 | Tanaka et al. |
| 8,932,239 | B2 | 1/2015 | Sokka et al. |
| 9,028,434 | B2 | 5/2015 | Tanaka |
| 9,049,783 | B2 | 6/2015 | Teofilovic |
| 9,061,131 | B2 | 6/2015 | Jahnke et al. |
| 9,144,694 | B2 | 9/2015 | Cain |
| 9,220,476 | B2 | 12/2015 | Coussios et al. |
| 9,220,574 | B2 | 12/2015 | Troesken et al. |
| 9,228,730 | B1 | 1/2016 | Inbody |
| 9,302,124 | B2 | 4/2016 | Konofagou et al. |
| 9,457,201 | B2 | 10/2016 | Hoelscher et al. |
| 9,526,923 | B2 | 12/2016 | Jahnke et al. |
| 9,636,133 | B2 | 5/2017 | Hall et al. |
| 9,642,634 | B2 | 5/2017 | Cain et al. |
| 9,763,688 | B2 | 9/2017 | Stulen et al. |
| 9,901,753 | B2 | 2/2018 | Cain et al. |
| 9,943,708 | B2 | 4/2018 | Roberts et al. |
| 10,046,179 | B2 | 8/2018 | Oskar-Kohler |
| 10,046,181 | B2 | 8/2018 | Barthe et al. |
| 10,058,352 | B2 | 8/2018 | Carvell et al. |
| 10,071,266 | B2 | 9/2018 | Cain |
| 10,130,828 | B2 | 11/2018 | Vortman et al. |
| 10,219,815 | B2 | 3/2019 | Maxwell et al. |
| 10,293,187 | B2 | 5/2019 | Cannata et al. |
| 10,293,374 | B2 | 5/2019 | Torashima et al. |
| 10,751,125 | B2 | 8/2020 | Levy et al. |
| 10,780,298 | B2 | 9/2020 | Cain et al. |
| 10,791,991 | B2 | 10/2020 | Burkett et al. |
| 10,799,209 | B2 | 10/2020 | Lahti et al. |
| 10,820,813 | B2 | 11/2020 | Alpert |
| 10,847,264 | B2 | 11/2020 | Mansker et al. |
| 10,869,603 | B2 | 12/2020 | Millett et al. |
| 10,869,633 | B2 | 12/2020 | Burkett |
| 10,869,648 | B2 | 12/2020 | Hubbard et al. |
| 10,874,353 | B2 | 12/2020 | Assif |
| 10,874,409 | B2 | 12/2020 | Matsubara et al. |

(56) References Cited

U.S. PATENT DOCUMENTS 10,888,232 B2 1/2021 Anderson et al.
10,893,808 B2 1/2021 Dorando
10,912,463 B2 2/2021 Davies et al.
10,925,688 B2 2/2021 Millett et al.
10,927,003 B2 2/2021 Millett et al.
10,932,678 B2 3/2021 Burkett
10,939,826 B2 3/2021 Glynn et al.
10,942,022 B2 3/2021 Johansson et al.
10,973,419 B2 4/2021 Corl
10,993,618 B2 5/2021 Mansker et al.
10,993,628 B2 5/2021 Tochterman
10,993,694 B2 5/2021 Meyer et al.
11,000,185 B2 5/2021 Stigall et al.
11,006,840 B2 5/2021 Stigall
11,013,491 B2 5/2021 Rice et al.
11,020,087 B2 6/2021 Hoffman
11,026,591 B2 6/2021 Burkett et al.
11,040,140 B2 6/2021 Unser et al.
11,058,399 B2 7/2021 Xu et al.
11,112,473 B2 9/2021 Assif
11,119,552 B2 9/2021 Spencer et al.
11,120,896 B2 9/2021 Balignasay et al.
11,135,454 B2 10/2021 Xu et al.
11,141,063 B2 10/2021 Kemp et al.
11,141,131 B2 10/2021 Stigall et al.
11,224,349 B2 1/2022 Davies et al.
11,234,649 B2 2/2022 Matsubara et al.
11,253,225 B2 2/2022 Hancock et al.
11,260,160 B2 3/2022 Matsubara et al.
11,272,845 B2 3/2022 Cheline et al.
11,298,030 B2 4/2022 Davies et al.
11,311,271 B2 4/2022 Stigall et al.
11,324,410 B2 5/2022 Burkett
11,350,906 B2 6/2022 Castella et al.
11,364,042 B2 6/2022 Maxwell et al.
11,406,498 B2 8/2022 Stigall et al.
11,413,017 B2 8/2022 Stigall et al.
11,432,900 B2 9/2022 Rakic et al.
11,648,424 B2 5/2023 Cannata et al.
11,701,134 B2 7/2023 Maxwell et al.
11,806,167 B2 11/2023 Burkett
11,813,484 B2 11/2023 Cannata et al.
11,813,485 B2 11/2023 Xu et al.
11,819,712 B2 11/2023 Cain et al.
11,864,918 B2 1/2024 Burkett et al.
11,872,412 B2 1/2024 Vortman et al.
11,890,025 B2 2/2024 Stigall et al.
11,980,778 B2 5/2024 Cannata et al.
12,144,677 B2 11/2024 Corl
12,343,198 B2 7/2025 Laroya
12,402,802 B2 9/2025 Vitek et al.
12,490,936 B2 12/2025 Corl
2001/0039420 A1 11/2001 Burbank et al.
2001/0041163 A1 11/2001 Sugita
2002/0045890 A1 4/2002 Celliers et al.
2002/0078964 A1 6/2002 Kovac et al.
2002/0099356 A1 7/2002 Unger et al.
2002/0145091 A1 10/2002 Talish et al.
2003/0092982 A1 5/2003 Eppstein
2003/0112922 A1 6/2003 Burdette et al.
2003/0149352 A1 8/2003 Liang et al.
2003/0157025 A1 8/2003 Unger et al.
2003/0169591 A1 9/2003 Cochran
2003/0181833 A1 9/2003 Faragalla et al.
2003/0199857 A1 10/2003 Eizenhofer
2003/0221561 A1 12/2003 Milo
2003/0236539 A1 12/2003 Rabiner et al.
2004/0127815 A1 7/2004 Marchitto et al.
2004/0138563 A1 7/2004 Moehring et al.
2004/0162571 A1 8/2004 Rabiner et al.
2004/0164213 A1 8/2004 Stephan
2004/0236248 A1 11/2004 Svedman
2004/0243021 A1 12/2004 Murphy et al.
2004/0249509 A1 12/2004 Rogers et al.
2004/0260214 A1 12/2004 Echt et al.
2005/0011296 A1 1/2005 Koseki
2005/0020945 A1 1/2005 Tosaya et al.
2005/0028289 A1 2/2005 Hakamiun
2005/0038339 A1 2/2005 Chauhan et al.
2005/0038361 A1 2/2005 Zhong et al.
2005/0119572 A1 6/2005 Angelsen et al.
2005/0121734 A1 6/2005 Degertekin et al.
2005/0152561 A1 7/2005 Spencer
2005/0154314 A1 7/2005 Quistgaard
2005/0154431 A1 7/2005 Quistgaard et al.
2005/0203399 A1 9/2005 Vaezy et al.
2005/0215901 A1 9/2005 Anderson et al.
2005/0234438 A1 10/2005 Mast et al.
2005/0283098 A1 12/2005 Conston et al.
2006/0058678 A1 3/2006 Vitek et al.
2006/0060991 A1 3/2006 Holsteyns et al.
2006/0074303 A1 4/2006 Chornenky et al.
2006/0089636 A1 4/2006 Christopherson et al.
2006/0173321 A1 8/2006 Kubota et al.
2006/0173387 A1 8/2006 Hansmann et al.
2006/0184166 A1 8/2006 Valle et al.
2006/0206028 A1 9/2006 Lee et al.
2006/0229659 A1 10/2006 Gifford et al.
2006/0241466 A1 10/2006 Ottoboni et al.
2006/0241523 A1 10/2006 Sinelnikov et al.
2006/0241533 A1 10/2006 Geller
2006/0264760 A1 11/2006 Liu et al.
2006/0293598 A1 12/2006 Fraser
2006/0293630 A1 12/2006 Manna et al.
2007/0004984 A1 1/2007 Crum et al.
2007/0010805 A1 1/2007 Fedewa et al.
2007/0016039 A1 1/2007 Vortman et al.
2007/0044562 A1 3/2007 Sarr
2007/0065420 A1 3/2007 Johnson
2007/0083120 A1 4/2007 Cain et al.
2007/0161902 A1 7/2007 Dan
2007/0167764 A1 7/2007 Hynynen
2007/0205785 A1 9/2007 Nilsson
2007/0219448 A1 9/2007 Seip et al.
2007/0239001 A1 10/2007 Mehl et al.
2007/0270683 A1 11/2007 Meloy
2007/0293762 A1 12/2007 Sawada et al.
2008/0013593 A1 1/2008 Kawabata
2008/0033297 A1 2/2008 Sliwa
2008/0033417 A1 2/2008 Nields et al.
2008/0051656 A1 2/2008 Vaezy et al.
2008/0055003 A1 3/2008 Unnikrishnan et al.
2008/0082026 A1 4/2008 Schmidt et al.
2008/0091125 A1 4/2008 Owen et al.
2008/0126665 A1 5/2008 Burr et al.
2008/0152867 A1 6/2008 Di Pede
2008/0154132 A1 6/2008 Hall et al.
2008/0167555 A1 7/2008 Qian et al.
2008/0177180 A1 7/2008 Azhari et al.
2008/0183076 A1 7/2008 Witte et al.
2008/0194965 A1 8/2008 Sliwa et al.
2008/0214964 A1 9/2008 Chapelon et al.
2008/0262345 A1 10/2008 Fichtinger et al.
2008/0262486 A1 10/2008 Zvuloni et al.
2008/0269614 A1 10/2008 Adachi et al.
2008/0283303 A1 11/2008 Cote
2008/0300485 A1 12/2008 Liu et al.
2008/0312561 A1 12/2008 Chauhan
2008/0319376 A1 12/2008 Wilcox et al.
2009/0012514 A1 1/2009 Moonen et al.
2009/0030339 A1 1/2009 Cheng et al.
2009/0036773 A1 2/2009 Lau et al.
2009/0099482 A1 4/2009 Furuhata et al.
2009/0112098 A1 4/2009 Vaezy et al.
2009/0171254 A1 7/2009 Kushculey et al.
2009/0198094 A1 8/2009 Fenster et al.
2009/0211587 A1 8/2009 Lawrentschuk
2009/0227874 A1 9/2009 Suri et al.
2009/0230822 A1 9/2009 Kushculey et al.
2009/0230823 A1 9/2009 Kushculey et al.
2009/0254008 A1 10/2009 Shields, Jr.
2009/0287083 A1 11/2009 Kushculey et al.
2009/0306502 A1 12/2009 Lacoste
2010/0011845 A1 1/2010 Laugham et al.

(56) References Cited

U.S. PATENT DOCUMENTS

| | | | |
|---|---|---|---|
| 2010/0042020 | A1 | 2/2010 | Ben-Ezra |
| 2010/0056924 | A1 | 3/2010 | Powers |
| 2010/0059264 | A1 | 3/2010 | Hasegawa et al. |
| 2010/0069797 | A1 | 3/2010 | Cain et al. |
| 2010/0125225 | A1 | 5/2010 | Gelbart et al. |
| 2010/0152624 | A1 | 6/2010 | Tanis et al. |
| 2010/0163694 | A1 | 7/2010 | Fadler et al. |
| 2010/0204578 | A1 | 8/2010 | Schmidt et al. |
| 2010/0210940 | A1 | 8/2010 | Bradley et al. |
| 2010/0241005 | A1 | 9/2010 | Darlington et al. |
| 2010/0251823 | A1 | 10/2010 | Adachi et al. |
| 2010/0255623 | A1 | 10/2010 | Huang |
| 2010/0261994 | A1 | 10/2010 | Davalos et al. |
| 2010/0274136 | A1 | 10/2010 | Cerofolini |
| 2010/0280374 | A1 | 11/2010 | Roberts et al. |
| 2010/0286518 | A1 | 11/2010 | Lee et al. |
| 2010/0286519 | A1 | 11/2010 | Lee et al. |
| 2010/0298744 | A1 | 11/2010 | Altshuler et al. |
| 2010/0305432 | A1 | 12/2010 | Duhay et al. |
| 2010/0317971 | A1 | 12/2010 | Fan et al. |
| 2010/0318002 | A1 | 12/2010 | Prus et al. |
| 2011/0072970 | A1 | 3/2011 | Slobodzian et al. |
| 2011/0112400 | A1 | 5/2011 | Emery et al. |
| 2011/0118600 | A1 | 5/2011 | Gertner |
| 2011/0118602 | A1 | 5/2011 | Weng et al. |
| 2011/0144490 | A1 | 6/2011 | Davis et al. |
| 2011/0144545 | A1 | 6/2011 | Fan et al. |
| 2011/0172529 | A1 | 7/2011 | Gertner |
| 2011/0178444 | A1 | 7/2011 | Slayton et al. |
| 2011/0208059 | A1 | 8/2011 | Cerofolini |
| 2011/0245671 | A1 | 10/2011 | Sato |
| 2011/0251528 | A1 | 10/2011 | Canney et al. |
| 2011/0257524 | A1 | 10/2011 | Gertner |
| 2011/0257561 | A1 | 10/2011 | Gertner et al. |
| 2011/0263967 | A1 | 10/2011 | Bailey et al. |
| 2011/0270136 | A1 | 11/2011 | Vitek et al. |
| 2011/0302719 | A1 | 12/2011 | Schwirian et al. |
| 2011/0319765 | A1 | 12/2011 | Gertner |
| 2011/0319927 | A1 | 12/2011 | Nita |
| 2012/0029337 | A1 | 2/2012 | Aoyagi |
| 2012/0029353 | A1 | 2/2012 | Slayton et al. |
| 2012/0029393 | A1 | 2/2012 | Lee |
| 2012/0046592 | A1 | 2/2012 | Albright et al. |
| 2012/0059264 | A1 | 3/2012 | Hope Simpson et al. |
| 2012/0059285 | A1 | 3/2012 | Soltani et al. |
| 2012/0065492 | A1 | 3/2012 | Gertner et al. |
| 2012/0065493 | A1 | 3/2012 | Gertner |
| 2012/0065494 | A1 | 3/2012 | Gertner et al. |
| 2012/0092724 | A1 | 4/2012 | Pettis |
| 2012/0101412 | A1 | 4/2012 | Vortman et al. |
| 2012/0111339 | A1 | 5/2012 | Barthe et al. |
| 2012/0130288 | A1 | 5/2012 | Holland et al. |
| 2012/0136279 | A1 | 5/2012 | Tanaka et al. |
| 2012/0158013 | A1 | 6/2012 | Stefanchik et al. |
| 2012/0172720 | A1 | 7/2012 | Asami et al. |
| 2012/0189998 | A1 | 7/2012 | Kruecker et al. |
| 2012/0215157 | A1 | 8/2012 | Berryman et al. |
| 2012/0232388 | A1 | 9/2012 | Curra et al. |
| 2012/0253176 | A1 | 10/2012 | Dumoulin |
| 2012/0259250 | A1 | 10/2012 | Sapozhnikov et al. |
| 2012/0271167 | A1 | 10/2012 | Holland et al. |
| 2012/0271223 | A1 | 10/2012 | Khanna |
| 2012/0281902 | A1 | 11/2012 | Oikawa et al. |
| 2013/0051178 | A1 | 2/2013 | Rybyanets |
| 2013/0053691 | A1 | 2/2013 | Kawabata et al. |
| 2013/0090579 | A1 | 4/2013 | Cain et al. |
| 2013/0102932 | A1 | 4/2013 | Cain et al. |
| 2013/0144165 | A1 | 6/2013 | Ebbini et al. |
| 2013/0144194 | A1 | 6/2013 | Ahn et al. |
| 2013/0172739 | A1 | 7/2013 | Paladini |
| 2013/0190623 | A1 | 7/2013 | Bertolina et al. |
| 2013/0190661 | A1 | 7/2013 | Wing et al. |
| 2013/0255426 | A1 | 10/2013 | Kassow et al. |
| 2013/0257224 | A1 | 10/2013 | Wodnicki et al. |
| 2013/0261467 | A1 | 10/2013 | Dausch et al. |
| 2013/0267853 | A1 | 10/2013 | Dausch et al. |
| 2013/0303906 | A1 | 11/2013 | Cain et al. |
| 2013/0338485 | A1 | 12/2013 | Mougenot et al. |
| 2014/0005521 | A1 | 1/2014 | Kohler et al. |
| 2014/0030806 | A1 | 1/2014 | Dudley et al. |
| 2014/0039358 | A1 | 2/2014 | Zhou et al. |
| 2014/0046181 | A1 | 2/2014 | Benchimol et al. |
| 2014/0058293 | A1 | 2/2014 | Hynynen et al. |
| 2014/0058294 | A1 | 2/2014 | Gross et al. |
| 2014/0073995 | A1 | 3/2014 | Teofilovic et al. |
| 2014/0074076 | A1 | 3/2014 | Gertner |
| 2014/0088613 | A1 | 3/2014 | Seo et al. |
| 2014/0100459 | A1 | 4/2014 | Xu et al. |
| 2014/0112107 | A1 | 4/2014 | Guo et al. |
| 2014/0128734 | A1 | 5/2014 | Genstler et al. |
| 2014/0180072 | A1 | 6/2014 | Davies |
| 2014/0180273 | A1 | 6/2014 | Nair |
| 2014/0200489 | A1 | 7/2014 | Behar et al. |
| 2014/0243664 | A1 | 8/2014 | El-Sayed et al. |
| 2014/0257145 | A1 | 9/2014 | Emery |
| 2014/0288428 | A1 | 9/2014 | Rothberg et al. |
| 2014/0316269 | A1 | 10/2014 | Zhang et al. |
| 2014/0324034 | A1 | 10/2014 | Assaf et al. |
| 2014/0330124 | A1 | 11/2014 | Carol |
| 2014/0378832 | A1 | 12/2014 | Sanghvi et al. |
| 2014/0378964 | A1 | 12/2014 | Pearson |
| 2015/0011875 | A1 | 1/2015 | Noordhoek et al. |
| 2015/0063668 | A1 | 3/2015 | You et al. |
| 2015/0073261 | A1 | 3/2015 | Kohler et al. |
| 2015/0080926 | A1 | 3/2015 | Emery |
| 2015/0148659 | A1 | 5/2015 | Vahala |
| 2015/0151141 | A1 | 6/2015 | Arnal et al. |
| 2015/0190121 | A1 | 7/2015 | Slayton et al. |
| 2015/0190659 | A1 | 7/2015 | Kolher |
| 2015/0196239 | A1 | 7/2015 | Meehan et al. |
| 2015/0224347 | A1 | 8/2015 | Barthe et al. |
| 2015/0257779 | A1 | 9/2015 | Sinelnikov et al. |
| 2015/0258352 | A1 | 9/2015 | Lin et al. |
| 2015/0265243 | A1 | 9/2015 | Kelly |
| 2015/0273246 | A1 | 10/2015 | Darlington et al. |
| 2015/0297177 | A1 | 10/2015 | Boctor et al. |
| 2015/0305710 | A1 | 10/2015 | Stigal et al. |
| 2016/0004933 | A1 | 1/2016 | Hu et al. |
| 2016/0038665 | A1 | 2/2016 | Schaefer et al. |
| 2016/0151618 | A1 | 6/2016 | Powers et al. |
| 2016/0184614 | A1 | 6/2016 | Matula et al. |
| 2016/0206867 | A1 | 7/2016 | Hossack et al. |
| 2016/0249859 | A1 | 9/2016 | Babkin et al. |
| 2016/0287909 | A1 | 10/2016 | Maxwell et al. |
| 2016/0331585 | A1 | 11/2016 | Kim |
| 2016/0339273 | A1 | 11/2016 | Al Mayiah |
| 2016/0354087 | A1 | 12/2016 | Noonan et al. |
| 2016/0361574 | A1 | 12/2016 | Barthe et al. |
| 2017/0000376 | A1 | 1/2017 | Partanen et al. |
| 2017/0042521 | A1 | 2/2017 | Popovic et al. |
| 2017/0049463 | A1 | 2/2017 | Popovic et al. |
| 2017/0071515 | A1 | 3/2017 | Chevillet et al. |
| 2017/0072227 | A1 | 3/2017 | Khokhlova et al. |
| 2017/0072228 | A1 | 3/2017 | Wang et al. |
| 2017/0079519 | A1 | 3/2017 | Sung et al. |
| 2017/0165046 | A1 | 6/2017 | Johnson et al. |
| 2017/0183062 | A1 | 6/2017 | Lee |
| 2017/0197099 | A1 | 7/2017 | Ruebel et al. |
| 2017/0232277 | A1 | 8/2017 | Hall et al. |
| 2019/0275353 | A1 | 9/2019 | Cannata et al. |
| 2020/0253550 | A1 | 8/2020 | Nair |
| 2020/0260964 | A1 | 8/2020 | Collins et al. |
| 2020/0330039 | A1 | 10/2020 | Burkett et al. |
| 2020/0330075 | A1 | 10/2020 | O'Reilly et al. |
| 2021/0000541 | A1 | 1/2021 | Levy et al. |
| 2021/0022703 | A1 | 1/2021 | Nair |
| 2021/0161398 | A1 | 6/2021 | Millett et al. |
| 2021/0353161 | A1 | 11/2021 | Merritt et al. |
| 2021/0401400 | A1 | 12/2021 | Sheehan et al. |
| 2022/0022845 | A1 | 1/2022 | Corl |
| 2022/0031287 | A1 | 2/2022 | Ebbini et al. |
| 2022/0079563 | A1 | 3/2022 | Kemp |
| 2022/0202483 | A1 | 6/2022 | Gertner |
| 2022/0219019 | A1 | 7/2022 | Xu et al. |

(56) References Cited

U.S. PATENT DOCUMENTS

| | | | |
|---|---|---|---|
| 2022/0257329 A1 | 8/2022 | Stigall et al. |
| 2023/0038498 A1 | 2/2023 | Xu et al. |
| 2023/0061534 A1 | 3/2023 | Stopek |
| 2023/0218930 A1 | 7/2023 | Stopek et al. |
| 2023/0240792 A1 | 8/2023 | Rakic et al. |
| 2023/0310899 A1 | 10/2023 | Hall et al. |
| 2023/0310900 A1 | 10/2023 | Cannata et al. |
| 2023/0329559 A1 | 10/2023 | Xu et al. |
| 2024/0000422 A1 | 1/2024 | Cort |
| 2024/0000426 A1 | 1/2024 | Davies et al. |
| 2024/0001157 A1 | 1/2024 | Cannata et al. |
| 2024/0001158 A1 | 1/2024 | Cannata et al. |
| 2024/0024705 A1 | 1/2024 | Xu et al. |
| 2024/0033542 A1 | 2/2024 | Cain et al. |
| 2024/0065632 A1 | 2/2024 | Burkett |
| 2024/0139552 A1 | 5/2024 | Duryea et al. |
| 2024/0139553 A1 | 5/2024 | Miller et al. |
| 2024/0149078 A1 | 5/2024 | Duryea et al. |
| 2024/0165666 A1 | 5/2024 | Hynynen et al. |
| 2024/0189267 A1 | 6/2024 | Bogott et al. |
| 2024/0189628 A1 | 6/2024 | Grumbir et al. |
| 2024/0207654 A1 | 6/2024 | Xu et al. |
| 2024/0225671 A9 | 7/2024 | Maxwell et al. |
| 2024/0269491 A1 | 8/2024 | Xu et al. |
| 2024/0285978 A1 | 8/2024 | Xu et al. |
| 2025/0128096 A1 | 4/2025 | Miller et al. |
| 2025/0186808 A1 | 6/2025 | Cannata et al. |
| 2025/0249289 A1 | 8/2025 | Miller et al. |
| 2025/0256132 A1 | 8/2025 | Xu et al. |
| 2025/0352828 A1 | 11/2025 | Miller et al. |
| 2025/0352831 A1 | 11/2025 | Cannata et al. |
| 2026/0115496 A1 | 4/2026 | Rootes et al. |

FOREIGN PATENT DOCUMENTS

| | | | |
|---|---|---|---|
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 102740777 | A | 10/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |
| CN | 106661535 | B | 3/2021 |
| CN | 113705586 | A | 11/2021 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 2887989 | B1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 2931130 | B1 | 10/2021 |
| EP | 2934304 | B1 | 10/2021 |
| EP | 3888534 | A1 | 10/2021 |
| EP | 3895604 | A1 | 10/2021 |
| EP | 3903672 | A1 | 11/2021 |
| EP | 2964096 | B1 | 12/2021 |
| EP | 3545829 | B1 | 3/2022 |
| EP | 3060129 | B1 | 4/2022 |
| EP | 2914166 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 2950737 | B1 | 1/2023 |
| EP | 2869804 | B1 | 2/2023 |
| EP | 2938265 | B1 | 2/2023 |
| EP | 4151156 | A1 | 3/2023 |
| EP | 2938271 | B1 | 4/2023 |
| EP | 4179995 | A2 | 5/2023 |
| EP | 2931132 | B1 | 7/2023 |
| EP | 2866733 | B1 | 9/2023 |
| EP | 3685874 | B1 | 10/2023 |
| EP | 2938255 | B1 | 11/2023 |
| EP | 3903672 | B1 | 11/2023 |
| EP | 2804525 | B1 | 6/2024 |
| ES | 2819552 | T3 | 4/2021 |
| ES | 2829822 | T3 | 6/2021 |
| GB | 2099582 | A | 12/1982 |
| IN | 387413 | B | 1/2022 |
| JP | 60-80779 | A | 5/1985 |
| JP | 61-196718 | A | 8/1986 |
| JP | S62144641 | A | 6/1987 |
| JP | S64068249 | A | 3/1989 |
| JP | H02104343 | A | 4/1990 |
| JP | 02-215451 | A | 8/1990 |
| JP | H02246961 | A | 10/1990 |
| JP | H0422351 | A | 1/1992 |
| JP | 06-197907 | A | 7/1994 |
| JP | 07-504339 | A | 5/1995 |
| JP | H07213527 | A | 8/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2008049199 | A | 3/2008 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2014204876 | A | 10/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 6785554 | B2 | 10/2020 |
| JP | 6979633 | B2 | 12/2021 |
| JP | 7171645 | B2 | 11/2022 |

(56) References Cited

FOREIGN PATENT DOCUMENTS

| | | | |
|---|---|---|---|
| RU | 2589649 | C1 | 7/2016 |
| WO | WO94/06355 | A1 | 3/1994 |
| WO | WO98/07373 | A1 | 2/1998 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2016/099279 | A1 | 6/2016 |
| WO | WO2018/208189 | A1 | 11/2018 |
| WO | WO2025/059671 | A1 | 3/2025 |

OTHER PUBLICATIONS

Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction +technologie+devices.pdf?folderid=db3a304412b407950112b408e8c90004&fileid=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain et al.; Concentric-ring and sector-vortex phased-array applicators for ultrasound hyperthermia; IEEE Transactions on Microwave Theory and Techniques; 34(5); pp. 542-551; May 1986.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focued ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Gateau et al.; Transcranial ultrasonic therapy based on time reversal of acoustically induced cavitation bubble signature. IEEE Transactions on Biomedical Engineering; 57(1); pp. 134-144; Sep. 18, 2009.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.

(56) References Cited

OTHER PUBLICATIONS

Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy: PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective, Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2, pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America, vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011 [retrieved on

(56) References Cited

OTHER PUBLICATIONS

Jan. 28, 2014] from: (http:/web.archive.org/web/20110720091822/http://www.histotripsy.umich.edu/index.html>.entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Cannata et al.; U.S. Appl. No. 18/311,050 entitled "Histotripsy systems and methods,", filed May 2, 2023.
Duryea et al.; U.S. Appl. No. 18/498,979 entitled "Histotripsy systems and methods,", filed Oct. 31, 2023.
Cannata et al.; U.S. Appl. No. 18/594,843 entitled "Histotripsy systems and methods,", filed Mar. 4, 2024.
Cannata et al.; U.S. Appl. No. 18/630,758 entitled "Histotripsy systems and methods,", filed Apr. 9, 2024.
Cannata et al.; U.S. Appl. No. 18/642,529 entitled "Histotripsy systems and associated methods including user interfaces and workflows for treatment planning and therapy,", filed Apr. 22, 2024.
Maxwell et al.; U.S. Appl. No. 18/737,731 entitled "Histotripsy for thrombolysis,", filed Jun. 7, 2024.
Stopek.; U.S. Appl. No. 18/761,937 entitled "Minimally invasive histotripsy systems and methods,", filed Jul. 2, 2024.
Shaffer et al.; U.S. Appl. No. 18/832,708 entitled "Histotripsy systems and methods,", filed Jul. 24, 2024.
Snell et al.; U.S. Appl. No. 18/886,807 entitled "Simulation software and tools for evaluating histotripsu therapy for a given pose and position of a therapy array,", filed Sep. 16, 2024.
Schell et al.; U.S. Appl. No. 18/890,580 entitled "Co-registration techniques between computed tomography imaging systems and histrotripsy robotic systems,", filed Nov. 14, 2024.
Cannata et al.; U.S. Appl. No. 18/812,761 entitled "Histotripsy systems and methods,", filed Aug. 22, 2024.
Lu et al.; Transcranial MR-guided histotripsy system; IEEE transactions on ultrasonics, ferroelectrics, and frequency control; 68(9); pp. 2917-2929; Mar. 23, 2021.
Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.
Wijlemans et al.; Magnetic resonance-guided high-intensity focused ultrasound (MR-HIFU) ablation of liver tumours; Cancer Imaging; 12(2); pp. 387-394; Sep. 28, 2012.
Miller; U.S. Appl. No. 19/103,752 entitled "Histotripsy systems and methods,", filed Feb. 13, 2025.
Hall et al. U.S. Appl. No. 19/229,825 entitled "Ultrasound transducer with transmit-receive capability for histotripsy,", filed Jun. 5, 2025.
Xu et al.; U.S. Appl. No. 19/006,948 entitled "Histotripsy therapy systems and methods for the treatment of brain tissue,", filed Dec. 31, 2024.
Cain et al.; U.S. Appl. No. 19/236,185 entitled "Histotripsy using very short ultrasound pulses,", filed Jun. 12, 2025.
Xu et al.; U.S. Appl. No. 19/471,955 entitled "Simultaneous MRI and ultrasound guidance for histotripsy systems and methods,", filed Oct. 2, 2025.
Xu et al.; U.S. Appl. No. 19/471,961 entitled "Real-time monitoring of histrotripsy dose delivery damage spatially and temporally,", filed Oct. 2, 2025.
Hall et al.; U.S. Appl. No. 19/475,240 entitled "Histotripsy systems and methods,", filed Oct. 14, 2025.
Maxwell et al.; U.S. Appl. No. 19/187,641 entitled "Histotripsy for thrombolysis,", filed Apr. 23, 2025.
Duryea et al.; U.S. Appl. No. 19/139,227 entitled "Systems and methods for enhancing histotripsy bubble cloud size through pulse shape optimization,", filed Jun. 13, 2025.
Cannata et al.; U.S. Appl. No. 19/329,331 entitled "Histotripsy systems and associated methods including user interfaces and workflows for treatment planning and therapy,", filed Sep. 15, 2025.
Kumar et al.; A comparative study of histotripsy parameters for the treatment of fibrotic ex-vivo human benign prostatic hyperplasia tissue; Research Square rs.3.rs-4549536.2; doi:10.21203/rs-4549536/v1; 24 pages; (Preprint); Jul. 2024.
Vlaisavljevich et al.; Histotripsy-induced caviation cloud initiation thresholds in tissues of different mechanical properties; IEEE Transactions on Ultrasonic, Ferroelectrics, and Frequency control; 61(2); pp. 341-352; 27 pages; (Author manuscript); Feb. 2014.
Vlaisavljevich et al.; Effects of tissue mechanical properties on susceptibility to histotripsy-induced tissue damage; Physics in Medicine and Biology; 59(2); pp. 253-270; 26 pages; (Author Manuscript); Jan. 2014.
Stopek; U.S. Appl. No. 19/361,539 entitled "Histotripsy systems and methods for rejected organ recovery", filed Oct. 17, 2025.
Coon et al.; HIFU treatment time reduction in superficial tumours through focal zone path selection; International journal of hyperthermia; 27(5); pp. 465-481; Aug. 1, 2011.

HISTOTRIPSY EXCITATION SEQUENCES OPTIMIZED FOR BUBBLE CLOUD FORMATION USING SHOCK SCATTERING

CROSS REFERENCE TO RELATED APPLICATIONS

This application is a continuation of U.S. patent application Ser. No. 16/410,821, filed May 12, 2019, which is a continuation of U.S. patent application Ser. No. 14/323,693, filed Jul. 3, 2014, now U.S. Pat. No. 10,293,187; which application claims the benefit under 35 U.S.C. 119 of U.S. Provisional Patent Application No. 61/842,820, filed Jul. 3, 2013, titled "Modulated Excitation Sequences for Enhanced Pulsed Ultrasound Cavitational Therapy", which applications are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to treating tissue with cavitation created by ultrasound therapy.

BACKGROUND

Histotripsy, or pulsed ultrasound cavitation therapy, is a technology where short, intense bursts of acoustic energy induce controlled cavitation (microbubble or bubble cloud formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high pressure amplitude acoustic pulses with low duty cycle.

Compared with conventional focused ultrasound technologies, Histotripsy has important advantages: 1) the destructive process at the focus is mechanical, not thermal; 2) bubble clouds appear bright on ultrasound imaging thereby confirming correct targeting and localization of treatment; 3) treated tissue appears darker (hypoechoic) on ultrasound imaging, so that the operator knows what has been treated; and 4) Histotripsy produces lesions in a controlled and precise manner. It is important to emphasize that unlike microwave, radiofrequency, or high-intensity focused ultrasound (HIFU), Histotripsy is not a thermal modality.

Early canine studies of Histotripsy homogenization of prostate tissue employed a therapy transducer that was positioned to deliver Histotripsy transabdominally. In these studies, the prostate was located only a short distance from the skin surface and there was a relatively wide path from the transducer through the skin to focus ultrasound energy. Consequently, the spherical Histotripsy therapy transducer employed in these studies had 14 cm aperture and 10 cm focal length (F-number=0.71). Histotripsy therapy transducers with high F-numbers have very low efficiency compared to transducers with low F-numbers. These inefficiencies are primarily due to nonlinear acoustic propagation leading to shockwave formation.

Specialized therapy transducer and drive electronics have been designed to focus Histotripsy therapy through the perineum to the prostate. One example of a therapy transducer 100 configured to deliver Histotripsy therapy to the prostate is shown in FIG. 1. The transducer 100 can comprise a plurality of ultrasound transducer elements 102 disposed within housing 104. The transducer can be connected to a waveform generator configured to deliver Histotripsy waveforms from the transducer to tissue. The prostate depth from this approach is significantly deeper than in the canine model above. Additionally, the skeletal anatomy of the pelvis and transrectal position of the ultrasound imaging probe significantly reduced the effective transducer aperture. A cut-out 106 in the lower perimeter of housing can be configured to accommodate an ultrasound imaging probe (not shown) which has an F-number=0.85 in the main diameter and F-number=0.98 at the cut out.

Based on bench-top experimentation and modeling, an initial set of therapy transducer excitation parameters (3 cycles/pulse, 750 Vpp, 500 Hz PRF (Pulse Repetition Frequency)) was selected for canine testing with this transducer. This excitation sequence produced a non-linear focal pressure waveform with a peak negative and peak positive pressure of approximately 25 MPa and 100 MPa in water. We define this sequence and its variants as a, standard, or non-optimized, sequence because the sequence parameters were not optimized for bubble cloud formation.

This standard excitation sequence and variants were used to treat approximately 30 canine subjects to establish feasibility, dosing (cumulative number of pulses), and treatment implementation guidelines. An additional 10 canine subjects were then treated in a confirmatory study. Although, these studies yielded outstanding efficacy results, the observation of apparent minor injury (subclinical fibrosis) to the prefocal abdominal rectus muscle in 2 of 10 subjects in the confirmatory trial led to the conclusion that the safety profile needed to be improved by developing Histotripsy pulse sequences that deliver energy more efficiently. It is likely that the need to improve the efficiency of Histotripsy will become more important as transducers are developed to go deeper into tissues through skeletal anatomical obstructions.

SUMMARY OF THE DISCLOSURE

Improved efficiency leading to pre-focal heat reduction is imperative when soft tissue is targeted deep beneath the skin surface through skeletal anatomical obstructions which require ultrasound therapy transducers that have relatively high F numbers (F-number>0.8). Sequences optimized for enhanced Histotripsy homogenization of soft tissues were developed to reduce the potential of pre-focal thermal injury by optimizing the sequence efficiency. Improved efficiency of optimized excitation sequences increases the probability of initiating Histotripsy bubble clouds in tissue and reduces the occurrences of extinguishing bubble clouds when translating through tissues. Additionally, optimized sequences can be designed to selectively ablate fibrous tissues or ablate less dense tissues while preserving more fibro-elastic vital structures such as neuro-vascular structures.

Effective optimized sequences for high F-number transducers are characterized by an initiation pulse which is designed to create a least a single acoustically generated nucleus (bubble), followed by a shock scattering pulse (hereafter referred to as a scattering pulse or scattering pressure waveform) after an optimized time delay to enable a shockwave to impinge upon the first bubble to create a bubble cloud. Subsequent scattering pulses can follow also with optimized timing in order to further maintain the effectiveness of the bubble cloud. Note that pulse and pressure waveform will be used interchangeably in this application.

A method of treating tissue with ultrasound energy, comprising the steps of delivering an initiation pressure waveform from an ultrasound therapy transducer into tissue, the initiation pressure waveform being configured to produce at least one bubble in the tissue, delivering a scattering pressure waveform from the ultrasound therapy transducer into the at least one bubble within a life-cycle of the at least one bubble, and producing cavitation nuclei near the at least one bubble with the scattering pressure waveform.

In some embodiments, the scattering pressure waveform is delivered within 5 μs to 200 μs of the initiation pressure waveform.

In one embodiment, the method further comprises repeating the delivering an initiation pressure waveform and delivering a scattering pressure waveform steps until treatment of the tissue is completed.

In one embodiment, a pressure amplitude and/or number of cycles of the initiation pressure waveform is minimized to reduce tissue heating.

In another embodiment, a peak-to-peak pressure of the scattering pressure waveform is sufficient in amplitude create additional cavitation nuclei in the focal region.

In alternative embodiments, the pressure amplitude and/or number of cycles of the scattering pressure waveform is minimized to reduce tissue heating.

In some embodiments the method further comprises, after delivering the scattering pressure waveform, delivering a second scattering pressure waveform towards the at least one bubble and the cavitation nuclei.

In some embodiments, the second scattering pressure waveform is delivered within 5 μs to 1 s of the scattering pressure waveform.

In another embodiment, the method further comprises delivering additional scattering pressure waveforms without delivering additional initiation pressure waveforms until the at least one bubble and/or the cavitation nuclei no longer remain in the tissue.

In some embodiments, the additional scattering pressure waveforms are delivered every 5 μs to 1 s.

In one embodiment, a pulse sequence comprising the initiation pressure waveform and the scattering pressure waveform has a sequence PRF ranging from 1-5000 Hz.

In other embodiments, the scattering pressure waveform delivers less energy to intervening tissue than the initiation pressure waveform.

In one embodiment, the initiation pressure waveform and the scattering pressure waveform have substantially similar pressure amplitudes. In another embodiment, a pressure amplitude of the scattering pressure waveform is less than a pressure amplitude of the initiation pressure waveform. In alternative embodiments, a pressure amplitude of the scattering pressure waveform is more than a pressure amplitude of the initiation pressure waveform.

A method of treating tissue with ultrasound energy is provided, comprising the steps of transmitting an initiation pressure waveform from an ultrasound therapy transducer into tissue, the initiation pressure waveform being configured to produce at least one bubble in the tissue, during a life-cycle of the at least one bubble, transmitting a scattering pressure waveform from the ultrasound therapy transducer into the at least one bubble, the scattering pressure waveform configured to become a shocked focal pressure waveform in the tissue having a shocked positive pressure half cycle and a shocked negative pressure half cycle, the shocked positive pressure half cycle being configured to impinge on the at least one bubble and to scatter, invert, and constructively interfere with the shocked negative pressure half cycle to form a negative pressure half cycle waveform, and producing cavitation nuclei near the at least one bubble with a shock scattering mechanism between the positive pressure half cycle waveform and the at least one bubble.

A method of delivering ultrasound energy to tissue is provided, comprising the steps of delivering an initiation pulse from an ultrasound therapy transducer configured to provide at least 5 MPa of peak negative pressure to produce at least one bubble in the tissue, delivering a first scattering pulse into the at least one bubble within 5 μs to 200 μs of the initiation pulse, and producing a cavitation cloud of nuclei near the at least one bubble with a shock scattering mechanism between the first scattering pulse and the at least one bubble.

An ultrasound therapy system is provided, comprising an ultrasound therapy transducer, and an ultrasound therapy generator coupled to the ultrasound therapy transducer, the ultrasound therapy generator configured to drive the ultrasound therapy transducer to deliver an initiation pressure waveform into tissue to produce at least one bubble in tissue, the ultrasound therapy generator being further configured to drive the ultrasound therapy transducer to deliver a first scattering pressure waveform within 5 μs to 200 μs of the initiation pressure waveform into the at least one bubble to produce cavitation nuclei near the at least one bubble.

In some embodiments, a peak to peak pressure of the first scattering pulse is sufficient in pressure amplitude to produce cavitation nuclei near the at least one bubble.

In other embodiments, the ultrasound therapy generator is further configured to drive the ultrasound therapy transducer to deliver at least one additional scattering pulse after the first scattering pressure waveform to produce cavitation nuclei near the at least one bubble.

In one embodiment, the ultrasound therapy generator further comprises a controller configured to generate complex waveforms to initiate the initiation and scattering pressure waveforms, a high voltage power supply coupled to the controller, an amplifier configured to receive and amplify the complex waveforms from the controller and high voltage power supply, and a matching network configured to match an impedance of the ultrasound therapy transducer to the amplifier.

A method of treating tissue with ultrasound energy is provided, comprising the steps of producing at least one bubble in the tissue with ultrasound energy, colliding a shocked focal pressure waveform with the at least one bubble, and forming cavitation nuclei near the at least one bubble.

In one embodiment, the colliding step is performed during a life-cycle of the at least one bubble.

In another embodiment, the colliding step is performed within 5 μs to 200 μs of the producing step.

In an alternative embodiment, the forming cavitation nuclei step is achieved with a shock scattering mechanism between the shocked focal pressure waveform and the at least one bubble.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Generation of Cavitation

Several principles of cavitation nuclei and bubble cloud formation that provide important background information for the development of the preferred embodiment are disclosed herein. Cavitation nuclei are individual bubbles formed as a result of the delivery of low pressure to tissue. Bubble clouds can comprise of dense clusters of cavitation nuclei that form at or near the transducer focus. The formation of cavitation nuclei (bubble clouds) are both key components of Histotripsy therapy.

Probability for Forming Cavitation Nuclei

Cavitation nuclei can be formed in tissue if the tissue is subjected to a peak negative (peak rarefaction) pressure approaching or exceeding the pressure level needed to create at least a single cavitation nucleus (bubble). Note that this level is variable and is dependent upon multiple factors including tissue properties (structure and composition, dissolved gas content, and existence of impurities), transducer geometry (focal distance and f number), and sequencing scheme (PRF; number of cycles). The number of cavitation nuclei formed from one acoustic pulse has been shown to be directly related to the peak negative pressure achieved.

Cavitation Time Course

Figure 1:
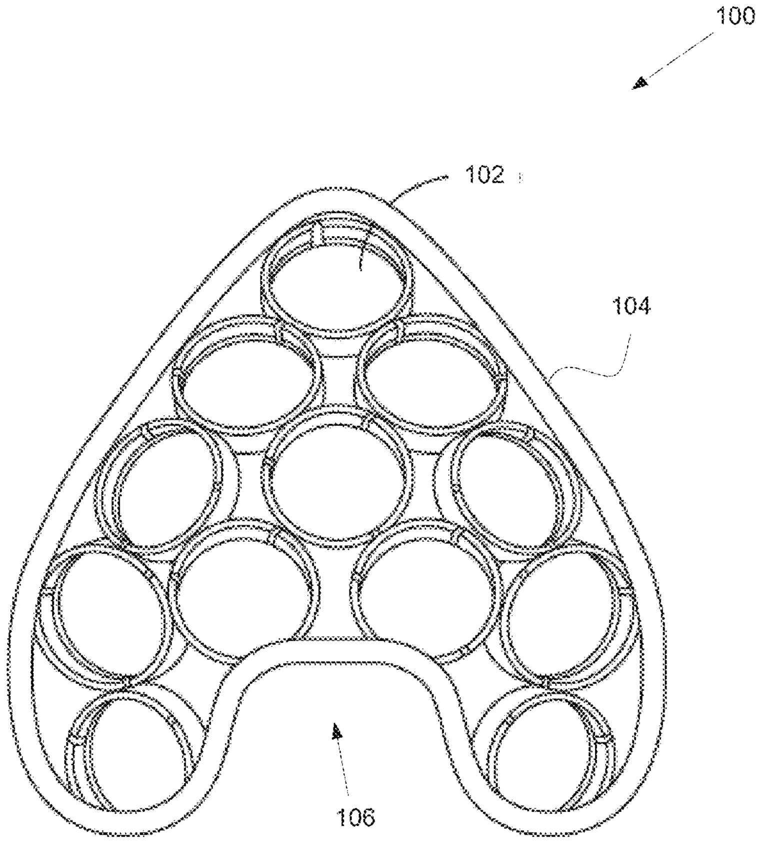
FIG. 1 is an ultrasound therapy transducer according to one embodiment.
Figures 2A, 2B, 2C:
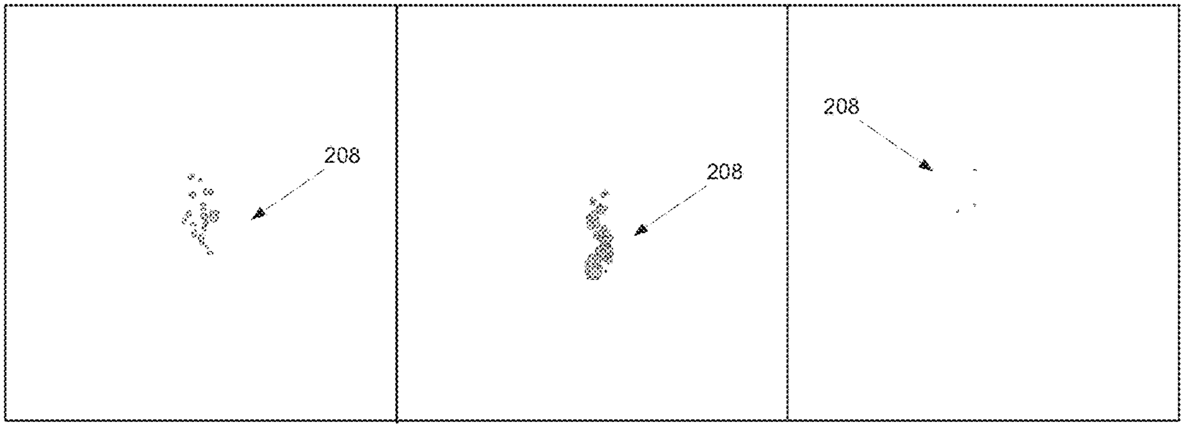
FIGS. 2*a*-2*c* are illustrations of bubble cloud initiation in water.

Cavitation nuclei grow to a maximum size and then collapse. The cavitation time course for the process of bubble initiation, growth, and then collapse is dependent on the medium (i.e., tissue type). The cavitation time course for liquids is longer than in gelatin and soft tissue. Table 1 compares cavitation initiation, growth, and collapse times in water vs. gelatin. FIGS. 2*a*-2*c* are illustrations showing a typical cavitation time course. FIG. 2*a* illustrates initiation of cavitation 208 in a medium, such as in tissue, in water, or in gelatin. FIG. 2*b* shows growth of the cavitation 208 to a maximum size, in which the cavitation bubbles are grouped together in the focal zone. FIG. 2*c* illustrates collapse of the cavitation 208 where nearly all the cavitation bubbles have collapsed and disappeared.

| Event/Delay-time | In Water (μs) | In Gelatin (μs) |
|---|---|---|
| Initiation | 68 | 68 |
| Growth | 149 | 84 |
| Collapse | 230 | 100 |

Figure 3:
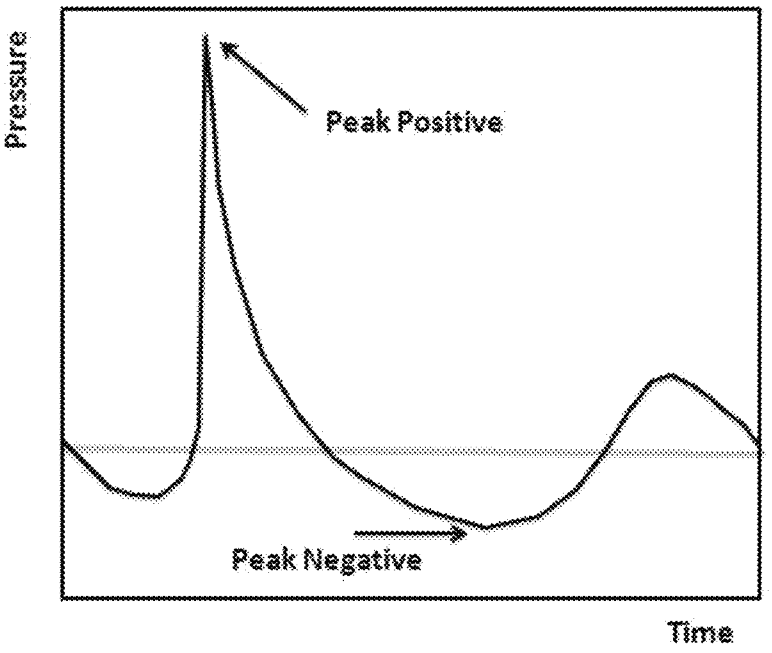
FIG. 3. illustrates a focal pressure waveform according to one embodiment.

Acoustic Shock and the Shock Scattering Mechanism for Bubble Cloud Formation As a sound waveform travels through the medium the positive (compression) half cycle(s) travel faster than the negative (rarefaction) half cycle(s). This effect causes the pressure waveform to become nonlinear creating a sharp transition between negative and positive half cycles of the pressure waveform. The pressure amplitude of the positive half cycle increases as the slope of this transition increases and the pressure waveform is said to be become more nonlinear or "shocked". This can be referred to as a shocked focal pressure waveform. The level of nonlinearity is dependent upon the pressure amplitude of the pressure waveform as well as the distance propagated through the medium. FIG. 3 shows an example of a shocked focal pressure waveform with a positive half cycle and a negative half cycle. It should be understood that shocked focal pressure waveforms can include a plurality of positive and negative half cycles.

According to the present disclosure, cavitation nuclei can be formed in tissue as a result of shock scattering. Shock scattering occurs when a shocked positive pressure half cycle of an acoustic waveform is reflected, or scattered, off of a pre-existing bubble(s) and the shocked positive pressure half cycle is consequently inverted such that it combines with the incident negative pressure half cycle of the acoustic waveform in an additive fashion. If this combined new negative pressure half cycle produced is large enough (i.e., above the intrinsic threshold for the tissue or medium of interest-greater than 5 MPa peak negative pressure for example), additional cavitation nuclei will form near any preexisting nuclei. This process repeats itself until the combined new negative pressure half cycle is not sufficient in pressure to create new cavitation nuclei.

FIGS. 4*a*-4*e* are conceptual drawings illustrating a shock scattering method of Histotripsy therapy. The frames on the top show a pre-existing bubble 408 and a shocked positive pressure half cycle 410, and the frames on the bottom show the ultrasound pulse pressure distribution 412 (horizontal line 414 indicates a pressure amplitude of zero). The pre-existing bubble 408 may be formed with an initiation pulse or sequence as described above. A shocked pressure waveform can then be transmitted towards the bubble 408 during a life-cycle of the bubble according to one embodiment of the shock scattering method.

Figure 4A:
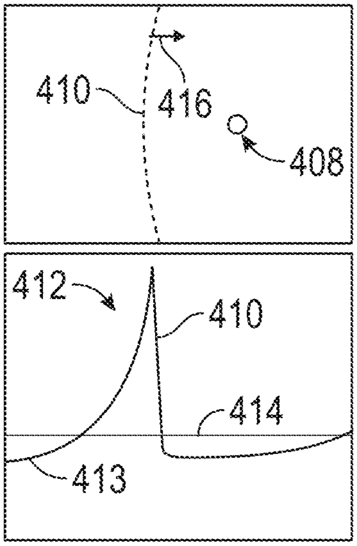
FIGS. 4*a*-4*e* are conceptual drawings that illustrate shock scattering.
Figure 4B:
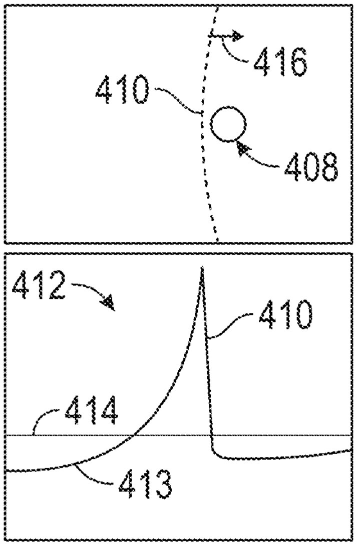
Figure 4C:
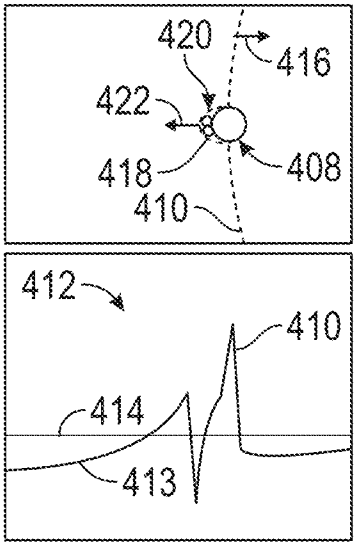
Figure 4D:
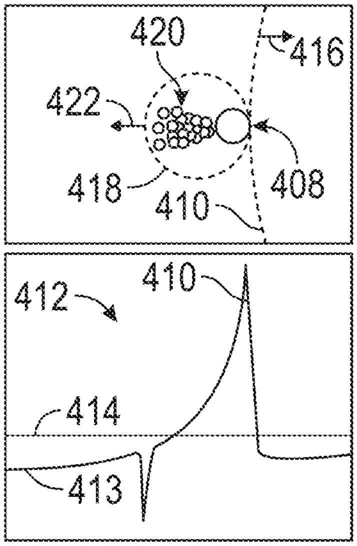
Figure 4E:
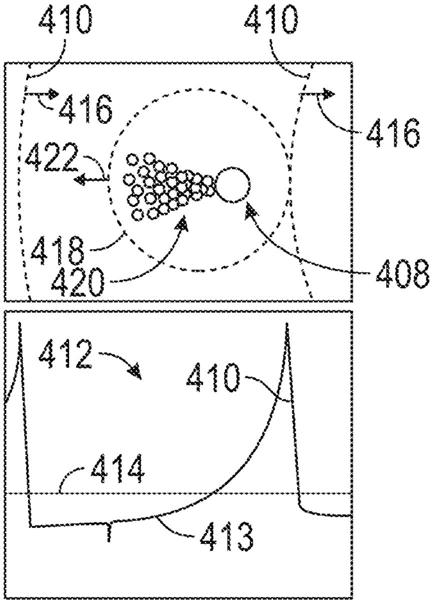

In FIGS. 4*a*-4*e*, the incident shocked pressure waveform 412 propagates from left to right towards the pre-existing bubble 408, as indicated by arrows 416. The incident shocked pressure waveform can be delivered towards and into the bubble during a life-cycle of the bubble, so that the incident shocked pressure waveform interacts with the bubble. A single pre-existing bubble 408 is shown in FIG. 4*a*, having already been generated in the tissue as described above. That bubble can expand in size, as shown in FIG. 4*b*, due to the initial negative pressure half cycle of the incident shocked pressure waveform. In FIG. 4*c*, a shocked positive pressure half cycle 410 of the incident shocked pressure waveform 412 impinges on the bubble 408 and the positive pressure half cycle begins to scatter. The scattered shocked positive pressure half cycle inverts and constructively interferes with the shocked negative pressure half cycle 413 of the incident shocked pressure waveform 412 to create a transient, large amplitude, negative pressure half cycle 418 (illustrated as the circular dotted line 418 in FIGS. 4*c*-4*e*) that produces additional cavitation nuclei 420 near or behind the bubble 408. The negative pressure half cycle 418 propagates from right to left, as indicated by arrows 422. The additional cavitation nuclei 420 form in the opposite direction of the shocked positive pressure waveform 410, until the negative pressure half cycle 418 drops below the threshold for the formation of cavitation nuclei, as shown in FIG. 4*e*. This process may be repeated with successive shocked pressure waveforms transmitted towards and into the pre-existing bubble 408 and additional cavitation nuclei 420.

Cavitation nuclei formed by this shock scattering method tend to grow towards the therapy transducer and their extent depends on the number of high pressure cycles in the pulse (waveform) and the pulse repetition frequency (PRF). Minimizing the number of cycles in a shocked waveform or reducing the sequence PRF are effective ways of reducing the length of the bubble cloud and also reducing the time average intensity and therefore the thermal dose.

Enhanced Bubble Cloud Formation Using Shock Scattering

The key components of a preferred Histotripsy excitation sequence described in this disclosure are: 1) A first pulse of the sequence, referred to as an initiation pulse or initiation pressure waveform, configured to form at least one bubble in the tissue 2) A second pulse of the sequence, referred to as a scattering pulse or scattering pressure waveform, configured to generate cavitation nuclei near the at least one bubble through shock scattering, and 3) A specific time delay between the initiation and scattering pulses.

The key parameters for the pulses are: The initiation pulse should be configured to produce at least one bubble in the tissue of interest. This can be achieved with a traditional Histotripsy initiation pulse, as described above, or with other ultrasound techniques that can induce bubble formation in tissue due to boiling such as HIFU or boiling Histotripsy. The scattering pulse should have a peak-to-peak pressure high enough for shock scattering formation of cavitation nuclei. In some embodiments, the time delay between these pulses can range between 5 μs and 200 μs. In another embodiment, the time delay between these pulses can range between 5 μs and 40 ms. In another embodiment, the time delay between these pulses can range between 5 μs and 1 s.

In another embodiment, the pressure amplitude and/or number of cycles used in the initiation pulse can be increased or decreased. Increasing the pressure amplitude and/or number of cycles in the initiation pulse may increase the probability of creating cavitation in the tissue. However this would also likely increase the time averaged intensity, and thermal dose, delivered to the tissue and the extent of the bubble cloud. Decreasing the pressure amplitude and/or number of cycles of the initiation pulse will reduce the intensity, and thermal dose, of the sequence but may limit the ability of the sequence to generate and/or maintain cavitation.

In another embodiment, the pressure amplitude and/or number of cycles used in the scattering pulse(s) can be increased or decreased. Increasing the pressure amplitude and/or number of cycles in the scattering pulse(s) may increase the probability of creating cavitation in the tissue. However this would also likely increase the time averaged intensity delivered to the tissue, and thermal dose, delivered to the tissue and the extent of the bubble cloud. Decreasing the pressure amplitude and/or number of cycles of the scattering pulse(s) will reduce the intensity, and thermal dose, of the sequence but may limit the ability of the sequence to generate and/or maintain cavitation.

The sequence PRF can be as high as 5000 Hz assuming that the time averaged intensity, and resultant thermal dose, are kept within safe limits. The preferred range depends on the tissues being treated. A higher PRF is recommended for more dense and fibrous tissues, and a low PRF is recommended for less dense tissues and for preservation of more fibrous and often vital tissues. Selective treatment of tissues with Histotripsy based on their stiffness can be a probable design and performance consideration for sequence development.

In some embodiments additional scattering pulses with lower pressure amplitude and/or number of cycles (compared with the initiation pulse pressure amplitude and/or number of cycles), can be applied in order to reduce the intensity, and thermal dose, of the sequence without reducing the sequence PRF.

Figure 5A:
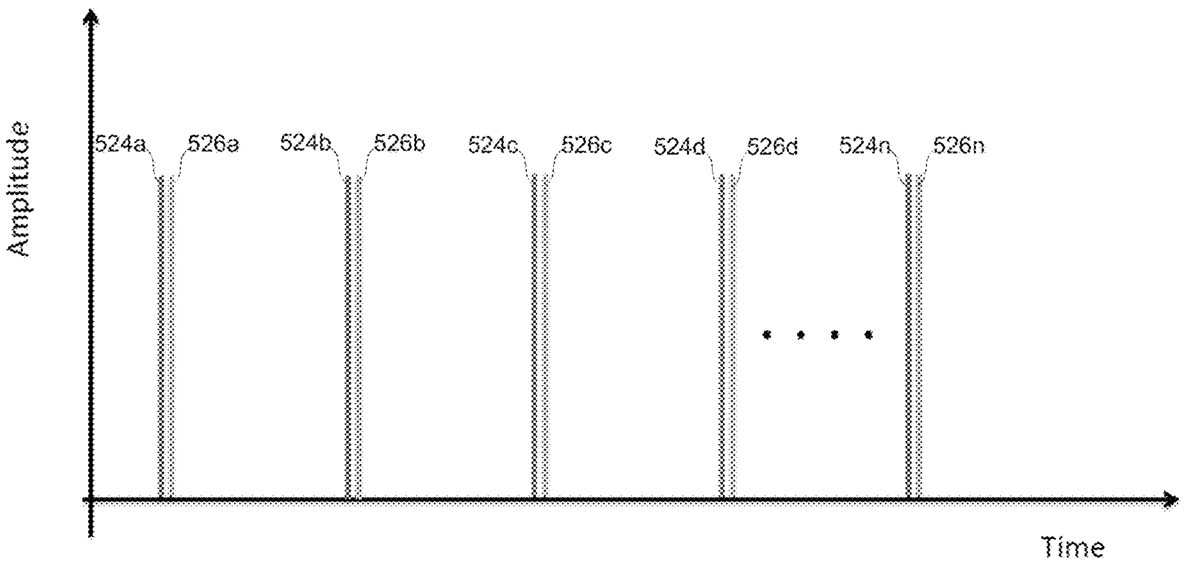
FIGS. 5*a*-5*c* illustrate various embodiments of pulse sequences that include initiation and scattering pressure waveforms for delivering ultrasound energy to tissue.
Figure 5B:
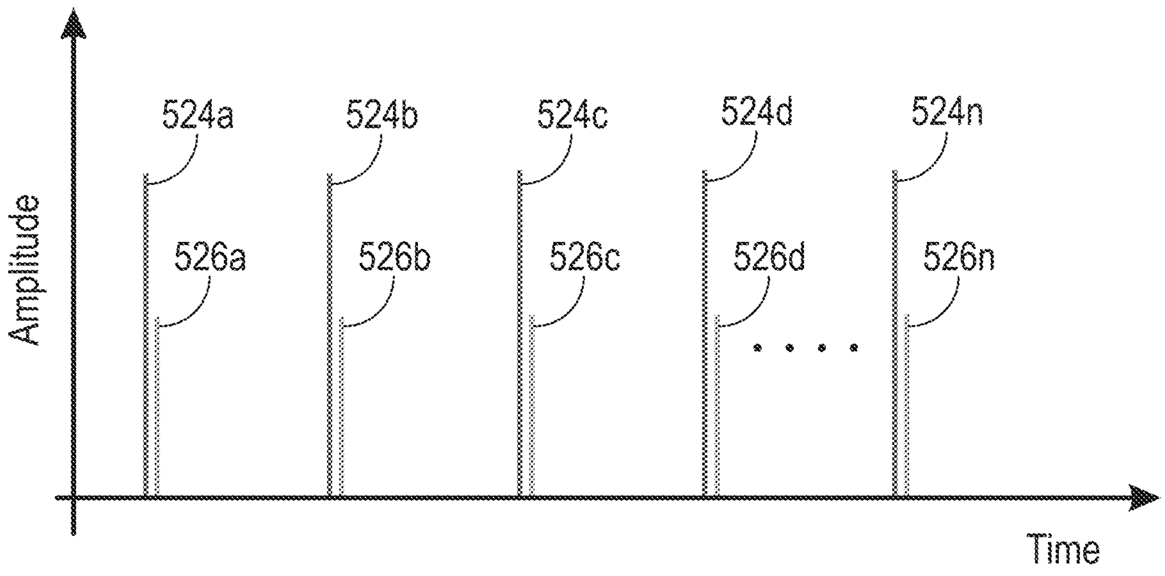
Figure 5C:
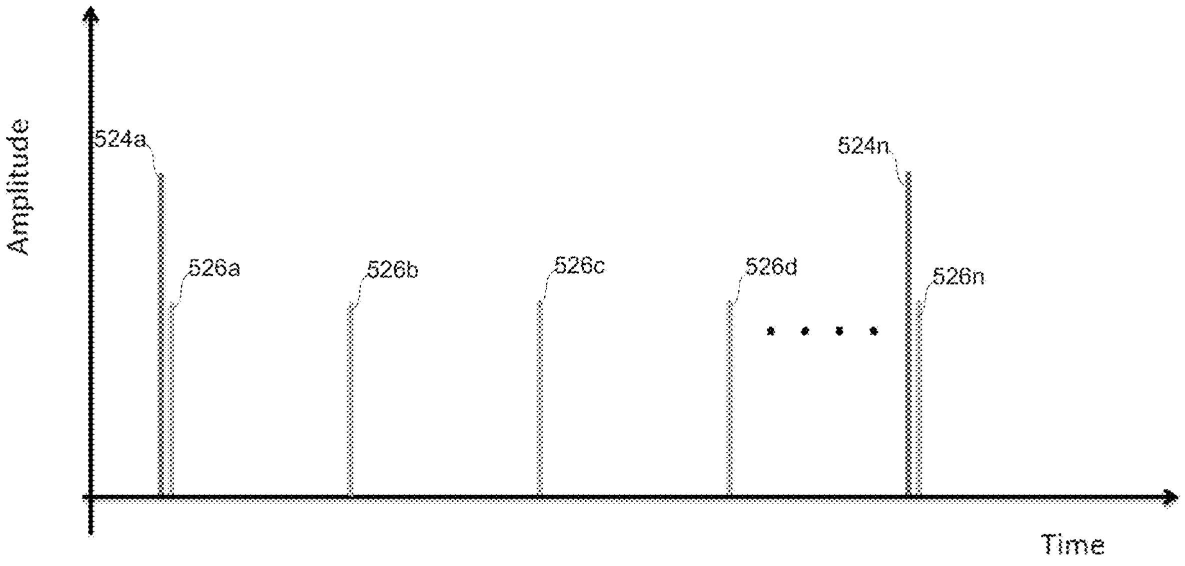

FIGS. 5*a*-5*c* illustrate three different embodiments for Histotripsy initiation and scattering pulse sequences that can be used to generate and maintain cavitation in tissue during a shocked scattering method of Histotripsy therapy. In FIG. 5*a*, an initiation pulse 524*a* comprising a pressure waveform configured to form at least one bubble in the tissue can be transmitted into tissue. After a specific time delay has passed, a scattering pulse 526*a* can be transmitted into tissue towards and into the at least one bubble formed by the initiation pulse 524*a*. In some embodiments, the specific time delay between these pulses can range between 5 μs and 200 μs. In another embodiment, the time delay between these pulses can range between 5 μs and 40 ms. In another embodiment, the time delay between these pulses can range between 5 μs and 1 s. The scattering pulse 526*a* becomes a shocked focal pressure waveform as it travels through the tissue, and the at least one shocked positive pressure half cycle of the scattering pulse impinges on the at least one bubble and is scattered by the at least one bubble. The shocked positive pressure half cycle of the scattering pulse inverts and constructively interferes with the shocked negative pressure half cycle of the scattering pulse to create a transient, large amplitude, negative pressure half cycle that produces additional cavitation nuclei behind the at least one bubble generated by the initiation pulse. These pulse sequence pairs of initiation and scattering pulses can be repeated to achieve the desired ablation effect in tissue from the resulting cavitation, as shown in FIG. 5*a* (pulse pairs 524*b*/526*b*, 524*c*/526*c*, 524*d*/526*d*, . . . , 524*n*/526*n*). In this embodiment, the pressure amplitudes and/or number of cycles of both the initiation and scattering pulses can be the same or approximately the same.

FIG. 5*b* shows another embodiment, similar to the embodiment of FIG. 5*a*, except the pressure amplitude of the scattering pulses 524*a*-524*n* are smaller than the pressure amplitude of the corresponding initiation pulses. Due to the principle of shock, the peak positive wave is amplified relative to the peak negative wave and therefore, the pressure amplitude used to create the scattering pulses can be lowered while still delivering the needed negative pressure with the reflected and inverted positive wave. This embodiment is more efficient than the embodiment of FIG. 5*a* and delivers a lower dose of energy into the tissue. In another embodiment, however, the pressure amplitude of the scattering pulses can be greater than the pressure amplitude of the corresponding initiation pulses.

FIG. 5*c* illustrates another embodiment, which is a variation of the embodiment of FIGS. 5*a* and 5*b*. In this embodiment, initiation pulse 524*a* is followed by a scattering pulse 526*a* after a specific time delay, but instead of following that with another initiation/scattering pulse pair as in FIG. 5*a*, instead the scattering pulse 526*a* is followed with another scattering pulse 526*b* after a second time delay. A plurality of scattering pulses can be delivered into tissue after the appropriate time delay to maintain the effectiveness of the bubble cloud (e.g., pulses 526*c*, 526*d*) to achieve the desired ablation effect in tissue from the resulting cavitation. The pressure amplitudes of the scattering pulse can be less than, equal to, or greater than the pressure amplitude of the initiation pulse. In some embodiments, the time delay for subsequent scattering pressure waveforms can be different than the time delay used for the first scattering pressure. For example, the first scattering pressure waveform may be delivered within 5 μs to 200 μs of the initiation pressure waveform, but subsequent scattering pressure waveforms may be delivered within 5 μs to 200 μs, 5 μs to 40 ms, or 5 μs to 1 s. If the cavitation needs to be re-initiated in the tissue, the sequence can be re-started with another initiation/scattering pulse pair, as shown by 524*n*/526*n* in FIG. 5*c*. This embodiment also uses a lower pressure amplitude scattering pulse, as in the embodiment of FIG. 5*b*, but also uses fewer initiation pulses. The result of this embodiment is the lowest dose of energy delivered to tissue between the embodiments of FIGS. 5*a*-5*c*. This strategy has the potential to lower the dose significantly (as much as 50% for example) compared with traditional histotripsy sequences.

Amplitude Reduction or Elimination of the Initiation Pulse Once the Bubble Cloud is Established The purpose of the initiation/scattering pair is to generate cavitation in tissue with shock scattering. Once the bubble cloud is generated, and if the focus is not moved, the initiation pulse may no longer be needed to maintain the effectiveness of the bubble cloud. In this case, the system could be designed to first create a bubble cloud with an initiation/scattering pair and follow that with lower pressure amplitude (relative to the initiation pulse pressure amplitude) scattering pulses until the focus is moved. At which point the process is repeated.

System Software and Hardware Design that Allowed for Sequence Development

Figure 6:
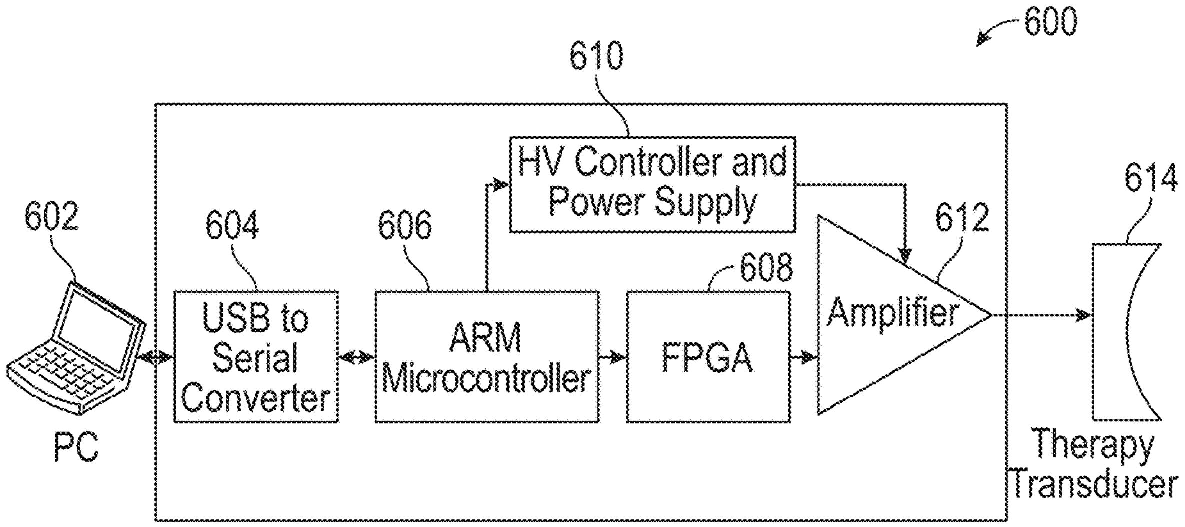
FIG. 6 illustrates a system configured to deliver the preferred sequences for treating the tissue with cavitation.

A Histotripsy system and generator is configured to generate very complex waveforms in order to support the ultrasound pulse sequences described herein. A simplified block diagram of system 600 is shown in FIG. 6. The main components of the system are: Computer/controller 602, USB to Serial Converter 604, Microcontroller 606, FPGA (Field Programmable Gate Array) 608, High Voltage Controller and Power Supply 610, Amplifier 612, and Therapy Transducer 614.

All controls for the generator can be established using "Histotripsy Service Tool" software that can run on the computer/controller 602 (e.g., a standard PC) and communicates to the generator via USB serial communication 604.

The system 600 is configured to receive multiple sets of different driving parameters and loop them, which give the ability to the user to create wide range of custom sequences where all parameters (PRF, voltage amplitude, number of cycles, number of pulses per set, frequency, transducer element channels enabled, and time delays) can be set differently for every pulse generated. Time delays between pulses can be specified by the PRF for a parameter set or by specifying zero as the number of cycles per pulse.

For overall voltage amplitude regulation, level of high voltage is changed accordingly through the Microcontroller 606 and HV Controller 610. This method cannot be used for dynamic voltage amplitude changes between two pulses since it will take too long for all capacitors on the HV line to discharge. For dynamic voltage amplitude changes between pulses, PWM (pulse width modulation) is used at the FPGA 608 where the duty cycle of the pulse is modulated in order to produce the desired pulse voltage and resultant pressure amplitude.

Histotripsy Service Tool

Histotripsy Service Tool is an application that can be run on any PC and is used for controlling the system. The Histotripsy Service Tool can start/stop the therapy, set and read the level of high voltage, therapy parameters (PRF, number of cycles, duty ratio, channel enabled and delay, etc), and set and read other service and maintenance related items.

USB to Serial Converter

USB to Serial converter 604 converts USB combination to serial in order to communicate to the Microcontroller 606.

Microcontroller

The Microcontroller 606 communicates to the computer/controller 602 (Histotripsy Service Tool) to set/read working parameters, start/stop the therapy, etc. It can use internal flash memory to store all the parameters. The Microcontroller communicates to the FPGA 608 all driving parameters that are necessary to generate complex pulsing. It also communicates using serial communication to the high voltage controller and power supply 610 where it can set/read the proper level of driving voltage.

FPGA

The FPGA 608 receives the information from the Microcontroller 606 and it generates the complex pulsing sequence that is required to drive the amplifier 612. The FPGA can run on 100 MHz clock since speed of pulsing is critical to be timed in 10 ns increments.

High Voltage Controller and Power Supply

The High Voltage Controller and Power Supply 610 receives the commands from the Microcontroller 606 regarding the level of DC voltage that needs to be supplied to the amplifier circuitry in order to have an adequate voltage amplitude level at the output of the amplifier.

Amplifier

The Amplifier 612 receives pulses generated by the FPGA and is supplied with high voltage from High Voltage Controller and Power Supply. It generates high voltage amplitude pulses that are fed to the Therapy Transducer 614 through the matching network components which properly matches the impedance of the therapy transducer to the impedance of the amplifier. It is necessary to use a large number of capacitors that can store enough energy to support peak current demand during the generation of high voltage amplitude pulses.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An ultrasound therapy system, comprising:

an ultrasound therapy transducer; and a waveform generator coupled to the ultrasound therapy transducer, the waveform generator being configured to drive the ultrasound therapy transducer to:

deliver a first pulse of a histotripsy excitation sequence into tissue, the first pulse comprising an initiation pressure waveform configured to produce at least one bubble in the tissue;

after a first time delay, deliver a second pulse of the histotripsy excitation sequence into tissue, the second pulse comprising a scattering pressure waveform configured to interact with the at least one bubble within a life-cycle of the at least one bubble and further to produce a cavitation nuclei near the at least one bubble;

after a second time delay different than the first time delay, repeat delivery of the first pulse of the histotripsy excitation sequence to produce at least one bubble in the tissue; and after a third time delay equal to the first time delay, repeat delivery of the second pulse of the histotripsy excitation sequence into the tissue to interact with the at least one bubble within a life-cycle of the at least one bubble and further to produce cavitation nuclei near the at least one bubble.

2. The system of claim 1, wherein the first time delay comprises 5 μs to 200 μs.

3. The system of claim 1, wherein the waveform generator is configured to drive the ultrasound therapy transducer to repeatedly deliver sequential pairs of the initiation pressure waveform and the scattering pressure waveform separated by the second time delay until treatment of the tissue is completed.

4. The system of claim 1, wherein a peak-to-peak pressure of the scattering pressure waveform is sufficient in amplitude to create additional cavitation nuclei in the focal region.

5. The system of claim 1, wherein the waveform generator is configured to drive the ultrasound therapy transducer to deliver a second scattering pressure waveform towards the at least one bubble and the cavitation nuclei after delivering the scattering pressure waveform.

6. The system of claim 1, wherein the histotripsy excitation sequence comprising the initiation pressure waveform and the scattering pressure waveform has a sequence pulse repetition frequency ranging from 1-5000 Hz.

7. The system of claim 1, wherein the scattering pressure waveform delivers less energy to intervening tissue than the initiation pressure waveform.

8. The system of claim 1, wherein the initiation pressure waveform and the scattering pressure waveform have similar pressure amplitudes.

9. The system of claim 1, wherein a pressure amplitude of the scattering pressure waveform is less than a pressure amplitude of the initiation pressure waveform.

10. The system of claim 1, wherein a pressure amplitude of the scattering pressure waveform is more than a pressure amplitude of the initiation pressure waveform.

* * * * *